United States Patent
Bowdish et al.

(10) Patent No.: US 7,598,030 B2
(45) Date of Patent: Oct. 6, 2009

(54) ANTIBODIES AGAINST CANCER PRODUCED USING MASKED CANCER CELLS AS IMMUNOGEN

(75) Inventors: Katherine S. Bowdish, Del Mar, CA (US); Hong Xin, Bonsall, CA (US); Toshiaki Maruyama, La Jolla, CA (US); Naveen Dakappagari, San Diego, CA (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 89 days.

(21) Appl. No.: 11/631,910

(22) PCT Filed: Jul. 8, 2005

(86) PCT No.: PCT/US2005/024261
§ 371 (c)(1), (2), (4) Date: Jul. 13, 2007

(87) PCT Pub. No.: WO2006/017174
PCT Pub. Date: Feb. 16, 2006

(65) Prior Publication Data
US 2007/0292428 A1    Dec. 20, 2007

Related U.S. Application Data

(60) Provisional application No. 60/586,812, filed on Jul. 10, 2004.

(51) Int. Cl.
*G01N 1/70* (2006.01)
*G01N 33/53* (2006.01)
*G01N 33/567* (2006.01)

(52) U.S. Cl. .............. 435/5; 435/7.1; 435/7.21; 435/69.6; 435/70.1; 435/70.2; 435/70.21

(58) Field of Classification Search .............. None
See application file for complete search history.

(56) References Cited

U.S. PATENT DOCUMENTS

| 4,902,615 A | 2/1990 | Freeman et al. | |
|---|---|---|---|
| 2003/0219821 A1 * | 11/2003 | Fisher et al. | 435/7.1 |

FOREIGN PATENT DOCUMENTS

| WO | WO95/06124 | * | 3/1995 |
|---|---|---|---|
| WO | WO-96/21671 | | 7/1996 |
| WO | WO96/21671 | * | 7/1996 |
| WO | WO96/40173 | * | 12/1996 |
| WO | WO03/019137 | * | 3/2003 |
| WO | WO-03/028625 | | 4/2003 |

OTHER PUBLICATIONS

Freeman, J.W., et al., "Masking of nontumorous antigens for development of human tumor nucleolar antibodies with improved specificity," Cancer Research, 45(11 Pt 2):5637-5642 (1985).
Su, Z-Z., et al., "Surface-epitope masking and expression cloning identifies the human prostate carcinoma tumor antigen gene PCTA-I a member of the galactin gene family," Proc. Natl. Acad. Sci. USA, 93:7252-7257 (Jul. 1996).

* cited by examiner

*Primary Examiner*—Karen A Canella
(74) *Attorney, Agent, or Firm*—Ropes & Gray LLP

(57) ABSTRACT

This disclosure relates to methods for selecting antibodies having desirable characteristics from a population of diverse antibodies. More specifically, this disclosure provides methods for identifying antibodies which bind to cancer cells, but which do not bind to human red or white blood cells or normal tissue cells. Antibodies of the disclosure can be used for therapeutic and/or diagnostic purposes.

13 Claims, No Drawings

ANTIBODIES AGAINST CANCER PRODUCED USING MASKED CANCER CELLS AS IMMUNOGEN

RELATED APPLICATIONS

This application is a national stage filing under 35 U.S.C. 371 of International Application PCT/US2005/024261, filed Jul. 8, 2005, which claims the benefit of U.S. Applications No. 60/586,812, filed on Jul. 10, 2004, the specification of which is incorporated by reference herein. International Application PCT/US2005/024261 was published under PCT Article 21(2) in English.

TECHNICAL FIELD

This disclosure relates to methods for selecting antibodies having desirable characteristics from a population of diverse antibodies. More specifically, this disclosure provides methods for identifying antibodies which bind to cancer cells, but which do not bind to human red or white blood cells or normal tissue cells.

BACKGROUND OF RELATED ART

Monoclonal antibody technologies have generated important tools for cancer diagnoses, therapeutics and prognoses. Generation of murine monoclonal antibodies with hybridoma technology, phage display, or other technologies is especially critical for both basic and clinical sciences. Anticancer monoclonal antibodies used in clinical applications, e.g. Herceptin and C225, were originally produced from mouse. They are beneficial to patients with solid tumors such as breast cancer, ovarian cancer, and head/neck cancers.

Much research has been done to identify antibodies that bind to surface molecules of cancer cells by whole-cell immunization followed by antibody screening. Although the theory of this approach is very attractive, not many therapeutic antibodies have been found after years of effort. This approach has proved difficult for several reasons.

One reason is that standard immunization procedures frequently fail to provide monoclonal antibodies with desired specificity because of the different immunogenicity of various antigen epitopes on the cells used for immunization. The immune response in favor of the more immunogenic epitopes or proteins is dominant. Traditional immunization usually results in generation of monoclonal antibodies to limited epitopes and immunodominant molecules.

Another difficulty with whole-cell immunization is that whole-cell immunization provides an efficient antigen concentration for limited surface molecules that have high antigen density, but a much lower effective antigen concentration for other surface molecules. Because of the complexity of surface antigens, traditional whole-cell immunization and screening may not produce a broad range of antibody specificities.

Also, cancer cells share many common surface antigens with normal cells, including red blood cells and white blood cells in the circulation. The immune response from a mouse may therefore not be tumor-specific although cancer cells are used as an immunogen. Phage display technology is a powerful tool to select tumor-specific antibodies. However, it is a challenge to select tumor-specific antibodies from animals such as mouse, rabbits, and chickens immunized with human cancer cells. In particular, antibodies against common antigens on both normal cells and cancer cells could severely interfere with screening for therapeutic anticancer antibodies, significantly decreasing the success of the whole cell panning approach. In fact, antisera from mice immunized with seven different cancer cell lines has been found to cross-react with human red blood cells (RBC). See Table 1. Therefore, screening for tumor-specific antibodies can be time-consuming and unproductive.

TABLE 1

FACS Analyses of Cross-reactivity of Anticancer Sera to Human Blood Cells

| Cell Lines | Cancer Type | Animal Number | FACS with Original Cancer Cells (Post-bleed/ Pre-bleed) Geo-Mean | FACS with RBC (Post-bleed/ Pre-bleed) Geo-Mean |
|---|---|---|---|---|
| MDA-MB-435 | Breast | 5 | 350 X | 149 X |
| MCF-7 | Breast | 5 | 300 X | 329 X |
| SK-OV3 | Ovarian | 5 | 178 X | 423 X |
| PC3 | Prostate | 4 | 400 X | 516 X |
| Du145 | Prostate | 5 | 420 X | 661 X |
| KM12L4a | Colon | 4 | 300 X | 307 X |
| A431 | Head and Neck | 3 | 275 X | 557 X |
| Caki-1 | Renal | 3 | 300 X | 160 X |

Subtractive immunization has been used to solve the problems described above. Subtractive immunization utilizes a distinct immune tolerization approach that can enhance the generation of monoclonal antibodies to desired antigens. Subtractive immunization is based on tolerizing the host animal to immunodominant or otherwise undesired antigens that may be structurally or functionally related to the antigens of interest. Tolerization of the host animal has been achieved through one of three methods: high zone, neonatal, or drug-induced tolerization. The tolerized animal is inoculated with the desired antigens and antibodies are generated in the subsequent immune response and are then screened for the desired reactivity. However, recent study suggested that neonatal "tolerization" induces immune deviation, not tolerance in the immunological sense. Neonates are not immune-privileged but generate $T_H2$ or $T_H1$ responses, depending on the mode of immunization. Chemical immunosuppression with cyclophosphamide has been the most effective subtractive immunization technique. As those skilled in the art will appreciate, normal cell immunization followed by cyclophosphamide treatment will kill all the proliferating immune cells reactive with normal cell antigens. However, this regimen also kills all of the helper T-cells required for B-cell maturation and differentiation. Therefore, when this regimen is followed by cancer cell immunization to elicit antibodies specific to tumor antigens, only low affinity antibodies of IgM isotype are produced.

It would be advantageous to have improved methods for identifying antibodies which bind to surface molecules of cancer cells but not to normal cells Improved methods for treating individuals suffering from cancer are also desirable.

SUMMARY

Antibodies that bind to cancer cells but not to human blood cells or normal cells are identified using masked cancer cells in the immunization process. A library of antibodies is created by immunization of a subject with cancer cells masked by contact with antisera from subjects previously immunized with normal (i.e., non-cancerous) human cells. Alternatively, the cancer cells are contacted with antibodies to epitopes on normal (i.e., non-cancerous) cells prior to immunization. The antibodies used for masking can be from any source, including for example antibodies from antisera or recombinantly produced antibodies. In some embodiments, antibody response to unmasked sub-dominant epitopes is optionally enhanced by modification of the masked cells with dinitrophenyl (DNP), a highly immunogenic hapten, which makes the cancer cells more easily recognized by the immune system. A library of antibodies produced in response to the unblocked, tumor-specific epitoptes on the masked cancer cells is generated. The library of antibodies can optionally be subjected to a negative selection process using normal cells. Then the library of antibodies is panned on cancer cells to identify antibodies that bind to the cancer cells, but show little to no binding to human blood cells or normal cells. These antibodies can be used for therapeutic and/or diagnostic purposes.

Thus, in one embodiment the present methods include the steps of collecting antiserum from non-human subjects immunized with non-cancerous human cells; contacting the antiserum with cancer cells to provide masked cancer cells; immunizing a subject with the masked cancer cells; and recovering antibodies that bind to the cancer cells from the subject.

In another embodiment of the present methods, cancer cells are contacted with one or more antibodies to receptors present on non-cancerous human cells to provide masked cancer cells; a subject is immunized with the masked cancer cells; and antibodies that bind to the cancer cells are recovered from the subject.

In certain embodiments, antibodies that bind to the cancer cells are recovered by generating an antibody library from subjects immunized with the masked cancer cells; removing antibodies that bind to human red and white blood cells and antibodies that bind to at least one other type of non-cancerous cell from the library; and then recovering from the library antibodies that bind to the cancer cell. In other embodiments, antibodies that bind to the cancer cells are recovered by collecting organs from subjects immunized with the masked cancer cells; generating hybridomas that express antibodies; and screening for antibodies that bind to the cancer cell but not to human red or white blood cells. In a particularly useful embodiment, the step of recovering antibodies that bind to cancer cells is achieved by generating a phage displayed antibody library using cells collected from subjects immunized with masked cancer cells; removing members of the library that bind to human blood cells to generate a sub-library; and recovering from the sub-library members that display antibodies that bind to the cancer cell.

DETAILED DESCRIPTION OF PREFERRED EMBODIMENTS

The present method to produce monoclonal antibodies utilizes masking immunization followed by phage display of antibodies and whole-cell panning for selection. This method takes advantage of the natural ability of the immune system to produce a secondary response to a previously encountered epitope by B-cell expansion and affinity maturation of antibodies. In the present methods, common epitopes on whole cancer cells and/or normal cells are blocked with antisera or specific antibodies to normal cells. The masked cells are then used for immunization. Usually, the immunization process is repeated several times. The continual blockage of the common epitopes prevents the secondary response to these epitopes from occurring, while unblocked epitopes specific to the cancer cells are capable of generating secondary responses. This allows even a small initial response to a lower density, less immunogenic but tumor-specific epitope to be amplified in each succeeding masking immunization. The presently described methods surmount many of the problems in traditional immunization. For therapeutic purposes, antibodies identified in accordance with the methods described herein should not have side effects on normal cells. This feature ensures the safety profile of the antibody for cancer therapy.

In certain embodiments, enhancement of antibody response to unmasked sub-dominant epitopes on the masked cancer cells is achieved by modification with a hapten, such as dinitrophenyl (DNP). DNP is a highly immunogenic hapten, which makes the cancer cells more easily recognized by the immune system. DNP is an aromatic compound (benzene ring with disubstituted nitro groups) that has the configuration of a hapten. A hapten is an antigenic determinant that is capable of binding to an antibody but incapable of eliciting an antibody response on its own but does when linked to a carrier protein. When the surface of cancer cell is coated with antibodies raised against normal cells, almost all of the dominant antigens are masked leaving only subdominant potentially low-density antigens for the activation of antibody response. Raising an effective immune response to these unmasked subdominant cancer specific antigens would be analogous to the scenario of "searching for a needle in haystack". One way to enhance the immunogenicity of these subdominant unmasked antigens is to modify them with DNP. DNP modified autologous cancer cell vaccines have been shown to elicit a robust immune response, which is characterized by delayed type hypersensitivity, release of proinflammatory cytokines such as IFN-γ and expansion of both CD4 and CD8 T cell subsets. DNP modification of low-density antigens preferentially attracts B-cells to the site of immunogen (masked cancer cell) and allow recognition and expansion of B-cells in response to DNP modified antigen. The process of B-cell trafficking to the immunogen and their subsequent expansion can be further aided by release of proinflammatory cytokines. DNP modification can be accomplished using techniques within the purview of those skilled in the art, such as those described in Berd, et al., J Clin Oncol 22:403 (2004); and Sojka, et al., Cancer Immunol Immunother 1:200 (2002).

As used herein, the term "antibodies" refers to complete antibodies or antibody fragments capable of binding to a selected target. Included are Fv, scFv, Fab' and F(ab')2, monoclonal and polyclonal antibodies, engineered antibodies (including chimeric, CDR-grafted and humanized, fully human antibodies, and artificially selected antibodies), and synthetic or semi-synthetic antibodies produced using phage display or alternative techniques. Small fragments, such as Fv and scFv, possess advantageous properties for diagnostic and therapeutic applications on account of their small size and consequent superior tissue distribution.

The present antibodies are identified by screening an antibody library. Antibodies can be raised in a subject, for example, by one or more injections of an immunizing agent and, if desired, an adjuvant. The immunizing agent in the present methods include any type of cancer cell or cancer cell fragments that have had epitopes thereon masked as described more fully hereinbelow. Typically, the immunizing agent and/or adjuvant will be injected in the subject by multiple subcutaneous or intraperitoneal injections and/or intravenous booster. Suitable adjuvants include, but are not limited to adjuvants that have been used in connection with cancer cell vaccines, such as, for example, unmethylated CpG motifs and *Bacillus* Calmette-Guerin (BCG). The immunization protocol may be selected by one skilled in the art without undue experimentation.

Any type of cancer cell can be used for immunizing a subject in accordance with the present methods. Suitable types of cancer cells include, but are not limited to melanoma, breast, ovarin, prostate, colon, head and neck, lung, renal, stomach, pancreatic, liver, bladder and brain. Cancer cells can be obtained from a variety of sources. For example, primary samples of cancer cells can be obtained directly from patients either through surgical techniques or biopsies. Cancer cells are also available from National Development and Research Institutes, Inc. ("NDRI"), New York, N.Y. Various types of cancer cells have also been deposited with and are available from American Type Culture Collection, Manassas, Va. ("ATCC") or other depositories, such as the National Cancer Institute. Where fragments of cancer cells (such as cell membranes or mitochondria) are to be used as the immunizing agent, techniques within the purview of those skilled in the art may be employed to disrupt the cancer cells and isolate suitable components for use in immunization.

Prior to immunization, a portion of the epitopes on the cancer cells are masked. Masking can be achieved using antisera from subjects immunized with human blood cells or normal (i.e., non-cancerous) human cells or, alternatively, with specific antibodies that are known to bind to receptors on human blood or normal cells. Given the guidance provided by the present disclosure, one skilled in the art will readily be able to determine suitable parameters for achieving masking without undue experimentation.

In certain embodiments, a pool of antibodies against normal cells is used to mask cancer cells during immunization, in order to decrease the cross-reactivity of anticancer sera to normal cells. Antisera is produced by immunizing a suitable subject with human red blood cells (RBCs), white blood cells (WBCs), total blood cells, normal tissue cells including normal cell lines or late-stage fetal tissue cells, or combinations of different types of normal cells. Human cancer cells are then incubated with antisera against normal cells to mask common surface molecules prior to use of the cancer cells in whole-cell immunization.

As those skilled in the art will appreciate, antiserum against normal cells may induce antibody-directed cellular cytotoxicity (ADCC) or complement-directed cytotoxicity (CDC) in vivo and cause cancer cell death, which could decrease the likelihood of success of masking immunization. In this case, a pool of Fab fragments is used to mask surface molecules. Fab fragments lack the Fc region, which is essential for ADCC and CDC.

There are at least two ways to achieve the surface masking using Fab fragments. In one embodiment Fab libraries from spleen, lymph nodes and bone marrow of subjects immunized with normal cells can be constructed. The Fab fragments are selected by several rounds of whole-cell panning of phage-displayed libraries on normal cells. A pool of selected Fab or scFv fragments is amplified and validated for binding to normal cells, and then used for masking immunization. One advantage of this process is that the selection pool should consist of antibodies against antigens with higher immunogenicity and density on normal cells.

In addition, the same pool of Fabs, scFv fragments and/or the $F(ab')_2$ prepared from serum IgG from mice immunized with normal cells can be used for in vitro epitope masking for deselecting binders to normal cells. The former is preferred as unlimited supply of antibodies for this purpose. For in vitro epitope masking, the pool of selected Fabs or the $F(ab')_2$ prepared from serum IgG from mice immunized with normal cells are mixed with target cancer cells prior to the incubation with library phage to block epitopes that are found on both cancer cells and normal cells. This ensures that Fabs that are selected by panning can only bind to cancer specific targets.

In another embodiment, Fabs can be generated by pepsin digestion of total IgG purified from antisera against normal cells. Fab and $F(ab')_2$ fragments can be purified after cleavage of the Fc region and then used for masking immunization.

Enhanced masking can be achieved by injecting additional antibody after cancer cell injection. For this purpose, additional Fab, scFv, or antisera can be injected 1-2 times every week intravenously.

Combinations of Fab or scFv fragments can also be used for masking immunization. These include, but are not limited to: purified antibodies previously selected in whole-cell panning, that bind to high density antigens (known or unknown) on red blood cells or normal cells; purified mouse IgG antibodies against normal cells. Other antibodies to receptors on normal cells will be known to those skilled in the art. In addition, Fab or scFv fragments against specific undesired targets can be included, such as antibodies against Her2/neu and EGF receptors. A single reagent of such an antibody or combination of different types of antibodies described here can be used to mask surface molecules before cancer cell immunization.

Once an immune response is elicited in the subject, antibodies may be collected for the selection process. Cells from tissue that produce or contain antibodies are collected from the subject, typically about three to five days after the last immunization. Suitable tissues include blood, spleen, lymph nodes and bone marrow.

Once the cells are collected, RNA is isolated therefrom using techniques known to those skilled in the art and a combinatorial antibody library is prepared. In general, techniques for preparing a combinatorial antibody library involve amplifying target sequences encoding antibodies or portions thereof, such as, for example the light and/or heavy chains using the isolated RNA of an antibody. Thus, for example, starting with a sample of antibody mRNA that is naturally diverse, first strand cDNA can be produced to provide a template. Conventional PCR or other amplification techniques can then be employed to generate the library. In certain embodiments, phage libraries expressing antibody Fab fragments (kappa or lambda light chains complexed to the IgG heavy chain fragment (Fd) are constructed in plasmid vectors using the methods described in U.S. application Ser. No. 10/251,085, the disclosure of which is incorporated herein in its entirety by this reference.

Antibodies that bind to cancer cells can then be selected from the library using techniques within the purview of those skilled in the art, such as, for example, whole cell panning, ELISA or FACS.

To help ensure that all antibodies that bind to normal cells are removed, human blood cells (either red or white or both), and optionally normal (i.e., non-cancerous) tissue cells are optionally used as absorbers in conducting stringent subtractions prior to screening of the library. Suitable human normal tissue cells for use in the subtraction process include endothelial cells, epithelial cells, smooth muscle cells, and other cells isolated from such tissues as liver, lung, heart, kidney, intestine, stomach, bladder, spleen, pancreas, bone marrow, brain, thymus, prostate, ovary, testis, skin, and the like. Suitable tissue can be obtained, for example, from normal donors, late stage of fetus, or from cell lines established from these tissues.

The subtractions can be performed by contacting the library of antibodies with the normal cells and then removing the normal cells along with any antibodies bound thereto. Removal of the cells can be achieved using any technique within the purview of those skilled in the art, such as centrifuging. The supernatant containing the unbound antibodies is retained as it is the portion that contains a sub-library of antibodies that bind to cancer cells but not to normal cells. To help ensure that all antibodies that bind to normal cells are removed, multiple rounds of subtraction can be performed. In particularly useful embodiments, at least three rounds of subtraction using red blood cells are performed. In other embodiments, multiple subtractions are conducted using at least two types of normal cells; namely, at least one type of blood cells and at least one other type of normal tissue cells. Preferably, the other normal tissue is derived from the same type of tissue as the cancer cells used for immunization. For example, if the subject was immunized with pancreatic cancer cells, then normal (i.e., non-cancerous) pancreatic tissue cells are used to perform the subtractions.

To provide adequate numbers of library members, the sub-library can be amplified between rounds of subtraction and/or prior to the screening for antibodies that bind to cancer cells. Techniques for amplification are within the purview of those skilled in the art.

After the negative selection process, antibodies derived from recombinant libraries may be selected using cancer cells, or polypeptides derived therefrom, to isolate the antibodies on the basis of target specificity. Suitable techniques for selecting antibodies that bind to cancer cells are within the purview of those skilled in the art.

Hybridoma methods can also be used to identify antibodies having the desired characteristics. Such techniques are within the purview off those skilled in the art. In a hybridoma method, a mouse, hamster, or other appropriate host animal, is typically immunized with cancer cells (masked as described hereinabove) to elicit lymphocytes that produce or are capable of producing antibodies that will specifically bind to the cancer cells. Alternatively, the lymphocytes may be immunized in vitro. The lymphocytes are then fused with an immortalized cell line using a suitable fusing agent, such as polyethylene glycol, to form a hybridoma cell (See, Goding, *Monoclonal Antibodies: Principles and Practice*, Academic Press, (1986) pp. 59-103; Kozbor, *J. Immunol.*, 133:3001 (1984); and Brodeur et al., *Monoclonal Antibody Production Techniques and Applications*, Marcel Dekker, Inc., New York, (1987) pp. 51-63 the disclosures of which are incorporated herein by this reference). The hybridoma cells are cultured in a suitable culture medium that preferably contains one or more substances that inhibit the growth or survival of the unfused, immortalized cells. The culture medium in which the hybridoma cells are cultured can then be assayed for the presence of monoclonal antibodies directed against the cancer cells using techniques within the purview of those skilled in the art and may be subjected to negative selection as described above. After the desired hybridoma cells are identified, the clones may be subcloned by limiting dilution procedures and grown by standard methods. Alternatively, the hybridoma cells may be grown in vivo as ascites in a mammal. The monoclonal antibodies secreted by the subclones are isolated or purified from the culture medium or ascites fluid by conventional immunoglobulin purification procedures.

The monoclonal antibodies that bind to cancer cells but show little or no binding to normal cells can be made by recombinant DNA methods that are within the purview of those skilled in the art. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells or phage (depending on the particular selection or screening method employed to identify the antibody) may serve as a preferred source of such DNA. Once isolated, the DNA may be placed into expression vectors, which are then transfected into host cells such as simian COS cells, Chinese hamster ovary (CHO) cells, NSO cells or other myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences or by covalently joining to the immunoglobulin coding sequence all or part of the coding sequence for a non-immunoglobulin polypeptide.

The present antibodies that bind to cancer cells but show little or no binding to normal cells in accordance with this disclosure may further include humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also include residues which are found neither in the recipient antibody nor in the imported CDR or framework sequences. In general, the humanized antibody will include substantially all of at least one, and typically two, variable domains, in which all or substantially all of the CDR regions correspond to those of one or more non-human immunoglobulins and all or substantially all of the FR regions are those of a human immunoglobulin consensus sequence. The humanized antibody optimally also will include at least a portion of an immunoglobulin constant region (Fc), typically that of a human immunoglobulin (Jones et al., *Nature,* 321:522-525 (1986); Riechmann et al., *Nature,* 332:323-329 (1988); and Presta, *Curr. Op. Struct. Biol.,* 2:593-596 (1992)).

Methods for humanizing non-human antibodies are well known in the art. Generally, a humanized antibody has one or more amino acid residues introduced into it from a source which is non-human. These non-human amino acid residues are often referred to as "donor" residues, which are typically taken from a "donor" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which all or some CDR residues and possibly some FR residues are substituted by residues from analogous sites in rodent antibodies.

In a further embodiment, there is provided a method for identifying proteins uniquely expressed in cancer cells employing antibodies in accordance with the present disclosure, by methods well known to those, skilled with art. In one method, Fab or scFv antigens are identified by immunoprecipitation and mass spectrometry. Specifically, in one such method to identify the antigens for these antibodies, scFvs are used to immunoprecipitate the antigens from lysates prepared from the microsomal fraction of cell-surface biotinylated cancer cells. Specifically, cancer cells are labeled with a solution of 0.5 mg/ml sulfo-NHS-LC-biotin in PBS, pH8.0 for 30 seconds. After washing with PBS to remove unreacted biotin, the cells are disrupted by nitrogen cavitation and the microsomal fraction is isolated by differential centrifugation. The microsomal fraction is resuspended in NP40 Lysis Buffer and extensively precleared with normal mouse serum and protein A sepharose. Antigens are immunoprecipitated with HA-tagged scFv antibodies coupled to Rat Anti-HA agarose beads. Following immunoprecipitation, antigens are separated by SDS-PAGE and detected by Western blot using streptavidin-alkaline phosphatase(AP) or by Coomassie G-250 staining. An antibody which does not bind to the cancer cells is used as a negative control. Antigen bands are excised from the Coomassie-stained gel and identified by mass spectrometry (MS). The immunoprecipitated antigens can also be identified by matrix assisted laser desorption ionization mass spectrometry (MALDI-MS) or microcapillary reverse-phase HPLC nano-electrospray tandem mass spectrometry (µLC/MS/MS). The antigens identified can then be used as an immunogen to elicit additional antibodies thereto using techniques within the purview of those skilled in the art.

The present antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

In other embodiments, bispecific antibodies are contemplated. Bispecific antibodies are monoclonal, preferably human or humanized, antibodies that have binding specificities for at least two different antigens. In the present case, one of the binding specificities is for a cancer cell, the other one is for any other antigen, and preferably for a cell-surface protein or receptor or receptor subunit.

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello, *Nature,* 305:537-539 (1983)). Antibody variable domains with the desired binding specificities (antibody-antigen-combining sites) can be fused to immunoglobulin constant domain sequences. The fusion preferably is with an immunoglobulin heavy-chain constant domain, including at least part of the hinge, CH2, and CH3 regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, for example, Suresh et al., *Methods in Enzymology,* 121:210 (1986); WO 96/27011; Brennan et al., *Science* 229:81 (1985); Shalaby et al., *J. Exp. Med.* 175:217- 225 (1992); Kostelny et al., *J. Immunol.* 148(5):1547-1553 (1992); Hollinger et al., *Proc. Natl. Acad. Sci. USA* 90:6444-6448 (1993); and Gruber et al., *J. Immunol* 152:5368 (1994); and Tutt et al., *J. Immunol.* 147:60 (1991).

The present antibodies can be administered as a therapeutic to cancer patients. Because the antibodies exhibit little to no binding to human blood cells or normal tissue cells, reduced side effects can be observed compared to other antibody therapies.

The present antibodies also may be utilized to detect cancerous cells in vivo. This is achieved by labeling the antibody, administering the labeled antibody to a subject, and then imaging the subject. Examples of labels useful for diagnostic imaging in accordance with the present disclosure are radiolabels such as $^{131}I$, $^{111}In$, $^{123}I$, $^{99m}Tc$, $^{32}P$, $^{125}I$, $^{3}H$, $^{14}C$, and $^{188}Rh$, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes, such as a transrectal probe, can also be employed. These isotopes and transrectal detector probes, when used in combination, are especially useful in detecting prostatic fossa recurrences and pelvic nodal disease. The antibody can be labeled with such reagents using techniques known in the art. For example, see Wensel and Meares, Radioimmunoimaging and Radioimmunotherapy, Elsevier, N.Y. (1983), which is hereby incorporated by reference, for techniques relating to the radiolabeling of antibodies. See also, D. Colcher et al., "Use of Monoclonal Antibodies as Radiopharmaceuticals for the Localization of Human Carcinoma Xenografts in Athymic Mice", Meth. Enzymol. 121: 802-816 (1986), which is hereby incorporated by reference.

A radiolabeled antibody in accordance with this disclosure can be used for in vitro diagnostic tests. The specific activity of a antibody, binding portion thereof, probe, or ligand, depends upon the half-life, the isotopic purity of the radioactive label, and how the label is incorporated into the biological agent. In immunoassay tests, the higher the specific activity, in general, the better the sensitivity. Procedures for labeling antibodies with the radioactive isotopes are generally known in the art.

The radiolabeled antibodies can be administered to a patient where it is localized to the tumor bearing the antigen with which the antibody reacts, and is detected or "imaged" in vivo using known techniques such as radionuclear scanning using e.g., a gamma camera or emission tomography. See e.g., A. R. Bradwell et al., "Developments in Antibody Imaging", Monoclonal Antibodies for Cancer Detection and Therapy, R. W. Baldwin et al., (eds.), pp. 65-85 (Academic Press 1985), which is hereby incorporated by reference. Alternatively, a positron emission transaxial tomography scanner, such as designated Pet VI located at Brookhaven National Laboratory, can be used where the radiolabel emits positrons (e.g., $^{11}C$, $^{18}F$, $^{15}O$, and $^{13}N$).

Fluorophore and chromophore labeled biological agents can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, Science, 162:526 (1968) and Brand, L. et al., Annual Review of Biochemistry, 41:843-868 (1972), which are hereby incorporated by reference. The antibodies can be labeled with fluorescent chromophore groups by conventional procedures such as those disclosed in U.S. Pat. Nos. 3,940,475, 4,289,747, and 4,376,110, which are hereby incorporated by reference.

The present antibodies can also be utilized to kill or ablate cancerous cells in vivo. This involves administering the antibodies bonded to a cytotoxic drug to a subject requiring such treatment. Since the antibodies recognize cancer cells, any such cells to which the antibodies bind are destroyed. Due to the use of the stringent subtraction technique, the amount of normal cells destroyed is minimal.

The antibodies of the present disclosure may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters. Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin, for example. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Procedures for conjugating the antibodies with the cytotoxic agents have been previously described.

Alternatively, the antibody can be coupled to high energy radiation emitters, for example, a radioisotope, such as $^{131}$I, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", Monoclonal Antibodies for Cancer Detection and Therapy, R. W. Baldwin et al. (eds.), pp 303-316 (Academic Press 1985), which is hereby incorporated by reference. Other suitable radioisotopes include α-emitters, such as $^{212}$Bi, $^{213}$Bi, and $^{211}$At, and β-emitters, such as $^{186}$Re and $^{90}$Y. Radiotherapy is expected to be particularly effective in connection with prostate cancer, because prostate cancer is a relatively radiosensitive tumor.

Where the antibodies are used alone to kill or ablate cancer cells, such killing or ablation can be effected by initiating endogenous host immune functions, such as complement-mediated or antibody-dependent cellular cytotoxicity.

The route of antibody administration (whether as the unaltered antibody or conjugated to a toxin or radioisotope) is in accord with known methods, e.g., injection or infusion by intravenous, intraperitoneal, intracerebral, intramuscular, subcutaneous, intraocular, intraarterial, intrathecal, inhalation or intralesional routes, or by sustained release systems. The antibody is preferably administered continuously by infusion or by bolus injection. One may administer the antibodies in a local or systemic manner.

The present antibodies may be prepared in a mixture with a pharmaceutically acceptable carrier. Techniques for formulation and administration of the compounds of the instant application may be found in "Remington's Pharmaceutical Sciences," Mack Publishing Co., Easton, Pa., latest edition. This therapeutic composition can be administered intravenously or through the nose or lung, preferably as a liquid or powder aerosol (lyophilized). The composition may also be administered parenterally or subcutaneously as desired. When administered systematically, the therapeutic composition should be sterile, pyrogen-free and in a parenterally acceptable solution having due regard for pH, isotonicity, and stability. These conditions are known to those skilled in the art.

Pharmaceutical compositions suitable for use include compositions wherein one or more of the present antibodies are contained in an amount effective to achieve their intended purpose. More specifically, a therapeutically effective amount means an amount of antibody effective to prevent, alleviate or ameliorate symptoms of disease or prolong the survival or the subject being treated. Determination of a therapeutically effective amount is well within the capability of those skilled in the art, especially in light of the detailed disclosure provided herein. Therapeutically effective dosages may be determined by using in vitro and in vivo methods.

In a further embodiment, recombinant DNA including an insert coding for a heavy chain variable domain and/or for a light chain variable domain of cancer-binding antibodies described hereinbefore are produced. The term DNA includes coding single stranded DNAs, double stranded DNAs consisting of said coding DNAs and of complementary DNAs thereto, or these complementary (single stranded) DNAs themselves.

Furthermore, DNA encoding a heavy chain variable domain and/or a light chain variable domain of the cancer-binding antibodies disclosed herein can be enzymatically or chemically synthesized DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an antibody directed to the cell line disclosed herein fused to a human IgG heavy chain constant domain, for example γ1, γ2, γ3 or γ4, preferably γ1 or γ4 are also provided. Recombinant DNAs including an insert coding for a light chain murine variable domain of an antibody directed to the cell line disclosed herein fused to a human constant domain κ or λ, preferably κ are also provided Another embodiment pertains to recombinant DNAs coding for a recombinant polypeptide wherein the heavy chain variable domain and the light chain variable domain are linked by way of a spacer group, optionally including a signal sequence facilitating the processing of the antibody in the host cell and/or a DNA coding for a peptide facilitating the purification of the antibody and/or a cleavage site and/or a peptide spacer and/or an effector molecule.

The DNA coding for an effector molecule is intended to be a DNA coding for the effector molecules useful in diagnostic or therapeutic applications. Thus, effector molecules which are toxins or enzymes, especially enzymes capable of catalyzing the activation of prodrugs, are particularly indicated. The DNA encoding such an effector molecule has the sequence of a naturally occurring enzyme or toxin encoding DNA, or a mutant thereof, and can be prepared by methods well known in the art.

In order that those skilled in the art may be better able to practice the compositions and methods described herein, the following examples are given for illustration purposes.

EXAMPLE 1

Masking the CD55 Antigen on Red Blood Cells and Human Prostate Cancer Cell Line PC3 with Antibody Fragment (Fab) L52-2

An anti-CD55 antibody (Fab L52-2) (produced as described in copending International Application No. PCT/US2005/024260 entitled "Methods For Discovering Antibodies Specific To Cancer Cells And Antibodies Discovered Thereby" filed under Express Mail Label No. EL983568264US on Jul. 8, 2005, the disclosure of which is incorporated herein in its entirety) was purified from E. coli ER2738 and bacterial endotoxin was removed to below 0.4 U/ml. The amino acid sequence of the Fab L52-2 was determined to be:

SRDNVLTQSPAIMSASPGEKVTMT-
CRASSSVGSSYLHWY.QKSGASPKLWI
YSTSKLASGVPARFSGSGSGTSYS-
LTISSVEAEDAATYYCQQYSGYPLTFG GGT-
KLEIKRADAAPTVSIFPPSSEQLTSG (SEQ ID NO: 1)

The truncated extra-cellular domain of CD55 was used in the validation of the masking immunization protocol. The reactivity of Fab L52-2 to CD55trTMD-His is confirmed by ELISA. Human red blood cells and prostate cancer cells (PC3 cells were used for whole-cell immunization. Both types of cells express high levels of CD55 on their cell surfaces). $3 \times 10^6$ cells were injected subcutaneously. A total of four subcutaneous injections at intervals of two weeks were performed. An intravenous bolus was added at the time of the last subcutaneous injection using the same quantity of cells. Four mice were used for each immunization group:

i. Group-1: Human RBCs alone
ii. Group-2: Human RBCs masked with L52-2
iii. Group-3: PC3 cells alone
iv. Group-4: PC3 cells masked with L52-2

Masking reactions were set up before each cell injection. Fab L52-2 at 300 nM was incubated with $3 \times 10^6$ cells at 4° C. for 30 minutes, which should be sufficient to block $10^6$ CD55 receptors on $3 \times 10^6$ cells.

After whole-cell immunization, the immune response and masking effects were evaluated by FACS analysis on RBCs and PC3 cells, and by ELISA using Fab L52-2. Because both types of cells share many common antigens on their cell surfaces, cross-reacting immune responses in mouse sera to both RBCs and PC3 cells was observed. For a successful immunization, FACS analysis on RBCs and PC3 cells gave the following results:

| v. | Group-1 (Human RBCs alone): | RBC (+), PC3(+) |
| vi. | Group-2 (Human RBCs masked with L52-2): | RBC (+), PC3(+) |
| vii. | Group-3 (PC3 cells alone): | RBC (+), PC3(+) |
| viii. | Group-4 (PC3 cells masked with L52-2): | RBC (+), PC3(+) |

Both types of cells injected express high levels of CD55 on their cell surfaces. To analyze the success of masking immunization, a competition ELISA using biotin-labeled Fab L52-2 is performed. Briefly, 96-well plates are coated with CD55trTMD-His antigen, and immunized sera are added to wells and incubated at different dilutions. Biotin-labeled Fab L52-2 is added to each well and incubated. Detection is achieved using methods within the purview of those skilled in the art. The sera from mice without Fab masking (Groups 1 and 3) competed well with Fab L52-2, whereas the sera from mice with Fab masking (Groups 2 and 4) will not compete, or competed only at high concentrations.

The success of masking immunization can also be analyzed with FACS. Briefly, RBCs or PC3 cells are incubated with or without immunized sera, then phycoerythrin (PE)-labeled Fab L52-2 is added to each reaction. Sera from the unmasked immunizations (Groups 1 and 3) bind to CD55 and therefore decreased subsequent binding to (PE)-labeled Fab L52-2, giving a decreased FACS signal. Sera from masked immunizations (Groups 2 and 4) bind weakly to cellular CD55, allowing strong binding of (PE)-labeled Fab L52-2 producing a strong FACS signal.

EXAMPLE 2

Mice were immunized with normal cells, including normal cell lines, normal cells isolated from normal donors and late stage fetal tissues, normal blood cells, RBCs and WBCs Serum titers were validated after immunization by FACS and whole-cell ELISA. Suitable tissue (spleen, lymph nodes and bone marrows) was collected for making Fab libraries. Antisera and/or Fab pools are used to do masking immunization. Fab libraries against normal cells are made, followed by several rounds of normal cell panning. Gene III is removed from the library DNA. Individual clones are tested on normal cells. The pool of positive clones are purified and used for masking immunization.

Separately, IgG from antisera is purified and digested with papain or pepsin. Fab or F(ab')$_2$ fragments are purified and used for masking immunization.

To achieve masking immunization, cancer cells are incubated with Fab, F(ab')$_2$, IgG, or antisera as described in the table below to achieve the maximum masking efficiency and best antibody response to unmasked antigens.

TABLE 2

Suggested Vaccine Formulations to be administered with a suitable adjuvant (e.g., CpG or BCG) known to enhance immune responses to whole cell vaccine

| Formulation | Comments |
| --- | --- |
| Tumor cells | Will induce antibodies to all antigens |
| Tumor cells + masking antibody | Will induce antibodies to unmasked antigens |
| Tumor cells + masking antibody + DNP modification[1] | Will focus the antibody response to subdominant antigens, however, masking antibodies will also be modified with DNP. In a syngeneic host, this may not be a problem |
| Tumor cells + DNP modification + masking antibody | All antigens will be modified with DNP; antibodies will mask dominant antigens. DNP may interfere with antibody masking |

[1]Established procedures can be used for DNP modification of cancer cells as detailed in Berd et al., J Clin Oncol, 22:403, 2004; and Sojka, et al., Cancer Immunol Immunother, 51:200, 2002

Cancer cells are injected after surface masking into Balb/c, C57BL6, or A/J mice. For enhanced masking, antibodies against normal cells are injected intravenously after cancer cell injection. As described above, four rounds of whole-cell immunization and masking are performed. Sera are collected from mice and evaluated by FACS and ELISA against cancer cells and normal cells to evaluate the immune response.

If the masking immunization is successful, spleen, lymph nodes, bone marrow and whole blood are collected from mice to make antibody libraries. Antibodies are selected by tumor whole cell panning and normal cell subtraction (RBCs, or total blood cells, or normal tissue cells). Screening procedures include but are not limited to: expression ELISA, whole-cell ELISA against cancer cells and normal cells, FACS with cancer cells and normal cells, immunohistochemical validation on normal and tumor tissue arrays, western analysis of tumor antigen with different cancer cell lines, tumor antigen identification by immunoprecipitation and mass spectrometry, cell based functional assays, analysis of tumor antigen intensity, analysis of antibody internalization, and other appropriate assays.

It will be understood that various modifications may be made to the embodiments disclosed herein. For example, as those skilled in the art will appreciate, any specific sequences described herein can be altered slightly without necessarily adversely affecting the functionality of the antibody or antibody fragment. For instance, substitutions of single or multiple amino acids in the antibody sequence can frequently be made without destroying the functionality of the antibody or fragment. Thus, it should be understood that antibodies having a degree of identity greater than 70% to any specific antibodies described herein are within the scope of this disclosure. In particularly useful embodiments, antibodies having a identity greater than about 80% to any specific antibodies described herein are contemplated. In other useful embodiments, antibodies having a identity greater than about 90% to any specific antibodies described herein are contemplated. Therefore, the above description should not be construed as limiting, but merely as exemplifications of preferred embodiments. Those skilled in the art will envision other modifications within the scope and spirit of the disclosure.

We claim:

1. A method comprising:
    collecting antiserum from non-human subjects immunized with non-cancerous human cells;
    contacting the antiserum with cancer cells to provide masked cancer cells;
    immunizing a subject with a composition comprising the masked cancer cells; and
    recovering antibodies that bind to the cancer cells from the subject,
    wherein the recovering step comprises
    a) generating an antibody library from subjects immunized with a composition comprising the masked cancer cells;
    b) removing from the library
        i) antibodies that bind to human red and white blood cells and
        ii) antibodies that bind to at least one other type of non-cancerous cell selected from the group consisting of endothelial cells, epithelial cells, smooth muscle cells, liver cells, lung cells, heart cells, kidney cells, intestine cells, stomach cells, bladder cells, spleen cells, pancreas cells, bone marrow cells, brain cells, thymus cells, prostate cells, ovary cells, testis cells and skin cells;
    and c) then recovering from the library antibodies that bind to the cancer cell.

2. A method comprising:
    collecting antiserum from non-human subjects immunized with non-cancerous human cells;
    contacting the antiserum with cancer cells to provide masked cancer cells;
    immunizing a subject with a composition comprising the masked cancer cells; and
    recovering antibodies that bind to the cancer cells from the subject,
    wherein the recovering step comprises
    a) collecting organs from subjects immunized with a composition comprising the masked cancer cells;
    b) generating hybridomas that express antibodies; and
    c) screening for antibodies that bind to the cancer cell but not to human red or white blood cells.

3. The method of claim 1 wherein the step of removing comprises:
    a) mixing human red blood cells with the library;
    b) removing the human red blood cells and antibodies bound thereto from the mixture and recovering a first portion of the library;
    c) mixing human red blood cells with the first portion of the library;
    d) removing the human red blood cells and antibodies bound thereto from the mixture and recovering a second portion of the library;
    e) mixing human red blood cells with the second portion of the library;
    f) removing the human red blood cells and antibodies bound thereto from the mixture and Recovering a third portion of the library; and
    g) recovering from the third portion of the library antibodies that bind to the cancer cell.

4. The method of claim 3 wherein the step of removing further comprises:
    mixing human white blood cells with at least one portion of the library and removing the human white blood cells and antibodies bound thereto from the mixture and recovering a portion of the library.

5. A method comprising:
    collecting antiserum from non-human subjects immunized with non-cancerous human cells;
    contacting the antiserum with cancer cells to provide masked cancer cells;

immunizing a subject with a composition comprising the masked cancer cells; and recovering antibodies that bind to the cancer cells from the subject, wherein the recovering step comprises:
a) generating a phage displayed antibody library using cells collected from subjects immunized with a composition comprising masked cancer cells;
b) removing members of the library that bind to human red blood cells to generate a sub-library; and
c) recovering from the sub-library members that display antibodies that bind to the cancer cell.

6. The method of claim 5 further comprising the step of removing members of the library that bind to normal tissue cells.

7. A method comprising:
contacting cancer cells with one or more antibodies to receptors present on non-cancerous human cells to provide masked cancer cells;
immunizing a subject with a composition comprising the masked cancer cells; and
recovering antibodies that bind to the cancer cells from the subject,
wherein the one or more antibodies to receptors known to be present on non-cancerous human cells are selected from the group consisting of complement receptors.

8. A method comprising:
contacting cancer cells with one or more antibodies to receptors present on non-cancerous human cells to provide masked cancer cells;
immunizing a subject with a composition comprising the masked cancer cells; and
recovering antibodies that bind to the cancer cells from the subject,
wherein the recovering step comprises
a) generating an antibody library from subjects immunized with a composition comprising the masked cancer cells;
b) removing from the library
  i) antibodies that bind to human red and white blood cells and
  ii) antibodies that bind to at least one other type of non-cancerous cell selected from the group consisting of endothelial cells, epithelial cells, smooth muscle cells, liver cells, lung cells, heart cells, kidney cells, intestine cells, stomach cells, bladder cells, spleen cells, pancreas cells, bone marrow cells, brain cells, thymus cells, prostate cells, ovary cells, testis cells and skin cells;
and c) then recovering from the library antibodies that bind to the cancer cell.

9. A method comprising:
contacting cancer cells with one or more antibodies to receptors present on non-cancerous human cells to provide masked cancer cells;
immunizing a subject with a composition comprising the masked cancer cells; and
recovering antibodies that bind to the cancer cells from the subject,
wherein the recovering step comprises
a) collecting organs from subjects immunized with a composition comprising the masked cancer cells;
b) generating hybridomas that express antibodies; and
c) screening for antibodies that bind to the cancer cell but not to human red or white blood cells.

10. The method of claim 8 wherein the step of removing comprises:
a) mixing human red blood cells with the library;
b) removing the human red blood cells and antibodies bound thereto from the mixture and recovering a first portion of the library;
c) mixing human red blood cells with the first portion of the library;
d) removing the human red blood cells and antibodies bound thereto from the mixture and recovering a second portion of the library;
e) mixing human red blood cells with the second portion of the library;
f) removing the human red blood cells and antibodies bound thereto from the mixture and recovering a third portion of the library; and
g) recovering from the third portion of the library antibodies that bind to the cancer cell.

11. The method of claim 10 wherein the step of removing further comprises:
mixing human white blood cells with at least one portion of the library and removing the human white blood cells and antibodies bound thereto from the mixture and recovering a portion of the library.

12. A method comprising:
contacting cancer cells with one or more antibodies to receptors present on non-cancerous human cells to provide masked cancer cells;
immunizing a subject with a composition comprising the masked cancer cells; and
recovering antibodies that bind to the cancer cells from the subject,
wherein the recovering step comprises:
a) generating a phage displayed antibody library using cells collected from subjects immunized with a composition comprising masked cancer cells;
b) removing members of the library that bind to human red blood cells to generate a sub-library; and
c) recovering from the sub-library members that display antibodies that bind to the cancer cell.

13. The method of claim 12 further comprising the step of removing members of the library that bind to normal tissue cells.

* * * * *